United States Patent
Zhang et al.

(10) Patent No.: US 10,058,525 B2
(45) Date of Patent: Aug. 28, 2018

(54) APPLICATION OF CHLOROGENIC ACID IN PREPARING MEDICINES FOR TREATING LUPUS ERYTHEMATOSUS

(71) Applicant: SICHUAN JIUZHANG BIOLOGICAL SCIENCE AND TECHNOLOGY CO., LTD., Chengdu, Sichuan (CN)

(72) Inventors: Jie Zhang, Sichuan (CN); Wang Huang, Sichuan (CN); Xiaoguang Chen, Sichuan (CN)

(73) Assignee: SICHUAN JIUZHANG BIOLOGICAL SCIENCE AND TECHNOLOGY CO., LTD., Chengdu, Sichuan (CN)

( * ) Notice: Subject to any disclaimer, the term of this patent is extended or adjusted under 35 U.S.C. 154(b) by 0 days.

(21) Appl. No.: 15/550,647

(22) PCT Filed: Jan. 26, 2016

(86) PCT No.: PCT/CN2016/072124
§ 371 (c)(1),
(2) Date: Aug. 11, 2017

(87) PCT Pub. No.: WO2016/127788
PCT Pub. Date: Aug. 18, 2016

(65) Prior Publication Data
US 2018/0021283 A1  Jan. 25, 2018

(30) Foreign Application Priority Data
Feb. 13, 2015 (CN) .......................... 2015 1 0078874

(51) Int. Cl.
*A61K 31/19* (2006.01)
*A61K 31/216* (2006.01)
*A61K 45/06* (2006.01)

(52) U.S. Cl.
CPC ............ *A61K 31/216* (2013.01); *A61K 45/06* (2013.01)

(58) Field of Classification Search
CPC ...................................................... A61K 31/19
USPC ......................................................... 514/570
See application file for complete search history.

(56) References Cited

U.S. PATENT DOCUMENTS

2011/0003018 A1\* 1/2011 Park ..................... A61K 36/355
424/725

FOREIGN PATENT DOCUMENTS

| CN | 102391119 A | 3/2012 |
| KR | 10-2014-0093435 A | 7/2014 |

\* cited by examiner

*Primary Examiner* — Raymond J Henley, III
(74) *Attorney, Agent, or Firm* — Novick, Kim & Lee, PLLC; Allen Xue

(57) ABSTRACT

The present invention provides an application of chlorogenic acid in preparing medicines for treating lupus erythematosus. The chlorogenic acid can improve an immunity function. The present invention provides a preparation for treating lupus erythematosus, comprising chlorogenic acid and pharmaceutically acceptable auxiliary materials. The present invention further provides a combined medicine comprising chlorogenic acid and medicines for treating lupus erythematosus.

8 Claims, 5 Drawing Sheets

APPLICATION OF CHLOROGENIC ACID IN PREPARING MEDICINES FOR TREATING LUPUS ERYTHEMATOSUS

TECHNICAL FIELD

The present invention relates to the application of chlorogenic acid in preparing medicines for treatment of lupus erythematosus, belonging to pharmaceutical field.

BACKGROUND ART

Chlorogenic acid (CGA), also named caffetannic acid and with the chemical name of 3-O-caffeoylquinic acid, is a carboxyl phenolic acid consisting of caffeic acid and quinic acid.

Chlorogenic acid, a metabolic product of aerobic respiration in plants, is a main active component distributing in many traditional Chinese materials, together with fruits and vegetables, possessing many biological activities, such as cardiovascular protective effects, antioxidation, anti-ultraviolet and anti-radiation, anti-mutagenesis and anti-cancer, antibacterial action, antivirus, reducing blood-lipid and blood-sugar, immunoregulation properties, etc. Chlorogenic acid is widely used in medicinal and chemical arts, as well as the field of food.

Lupus erythematosus (LE) is a typical autoimmunity connective tissue disorders, particularly among 15-40 years of females. Lupus erythematosus is a spectrum of disease, including discoid lupus erythematosus (DLE), subacute cutaneous lupus erythematosus (SCLE), systemic lupus eythematosus (SLE), lupus erythematosus profundus (LEP), neonatal lupus erythematosus (NLE), drug-induced lupus (DIL), and so on.

Currently, lupus erythematosus is treated in clinical by mainly using antimalarials (such as hydroxychloroquine), thalidomide or a small dose of oral hormone. At present, medicines for treatment of lupus erythematosus in traditional Chinese medicine includes compound rehmannia decoction, composing of *Rehmanniadride*, gypsum, *Caulis lonicerae* stem, that has effects of eliminating heat by nourishing yin and cooling blood, and mainly is used for treating patients with mild and moderate active stage of systemic lupus erythematosus; also includes lupus pills, whose formula contains a dozen of crude medicines, such as *Lonicera japonica Thunb*, *Forsythia suspense*, *Taraxacum-mongolicum*, *Coptischinensis*, *Rehmanniaglutinosa*, *Rheum officinaleBaill*, *Glycyrrhizauralensis*, centipede, and others, having effects of clearing away the heat evil and expelling superficial evils, cooling blood, promoting blood circulation by removing blood stasis, increasing cellular immune function, improving disease resistance of organisms, decreasing circulation immune complex, and said pills are used for treatment of systemic lupus erythematosus. However, compound formula of Chinese medicines has complicated constituents, and active ingredients are not confirmed, and the mechanism of action is not definite, with a certain potential safety hazard. Thus, there is an urgent need for singular effective constituent used for treatment of lupus erythematosus.

CONTENTS OF THE INVENTION

Focusing on above technical problems, the object of the present invention is to provide a new use of chlorogenic acid.

Above object of the present invention is realized by following technical solution: an application of chlorogenic acid in preparation of medicines for treatment of lupus erythematosus.

In the present invention, inventors have unexpectedly found that the water extract and alcoholic extract of eucommia leaves show obviously inhibitory actions on lupus erythematosus during screening medicines for treatment of lupus erythematosus; further screening of potency constituents indicates that chlorogenic acid, geniposidic acid, and aucubin have relatively obvious inhibition on lupus erythematosus, and especially chlorogenic acid has a more obvious inhibition. The present invention realizes the purpose of treating lupus erythematosus by improving immune function via chlorogenic acid.

In the present invention, preferably, said medicaments are prepared by chlorogenic acid as active components, with addition of pharmaceutically acceptable excipients or auxiliary materials.

Additional object of the present invention is to provide a preparation used for treatment of lupus erythematosus, and said medicaments contain chlorogenic acid and pharmaceutically acceptable excipients or auxiliary materials. Said excipients or auxiliary materials include, but are not limited to, mannitol, sodium bisulfite, starch, dextrin powder, absolute alcohol, injectable water, sugar powder, lactose, hydroxypropylmethylcellulose, magnesium stearate, sucrose, Povidone K30.

In the present invention, said preparations may be oral preparations, injectable preparations, or transdermal preparations for external use. Preferably, the preparations according to the present invention contain 1-1000 mg of chlorogenic acid per dose unit, and the dosage used in clinical is 1-100 mg/kg.

Further object of the present invention is to provide a drug combination used for treatment of lupus erythematosus, and said combination includes chlorogenic acid and other medicines treating lupus erythematosus. Preferably, said medicines treating lupus erythematosus include, but are not limited to, hydroxychlorochin, methopterin, azathioprine, clofazimine, thymosin, levamisole, and prednisone.

Experiments of the present invention indicates chlorogenic acid can ameliorate the pathological change of lupus erythematosus models, have immuno-regulation actions, and improve immune functions, that provides a theoretical basis for treatment of lupus erythematosus in clinical.

Beneficial effects of the present invention is to provide a medicament for prevention and treatment of lupus erythematosus, that realizes the purpose of prevention and treatment by improving immune functions of organisms.

1): when treated by high dose of chlorogenic acid for 14 days, for ENA polypeptide antibodies, anti-Sm, anti-ssA and anti-ssB bodies are positive;
2): when treated by middle dose of chlorogenic acid for 14 days, for ENA polypeptide antibodies, anti-Sm, anti-Rib, anti-ssA and anti-ssB bodies are positive;
3): when treated by low dose of chlorogenic acid for 14 days, for ENA polypeptide antibodies, anti-Sm, anti-ssA and anti-ssB bodies are positive;
4): when treated by artesunate for 14 days, for ENA polypeptide antibodies, anti-Sm, anti-ssA and anti-ssB bodies are positive;

5): when treated by prednisone for 14 days, for ENA polypeptide antibodies, anti-Sm, anti-ssA and anti-ssB bodies are positive.

Figure 1:
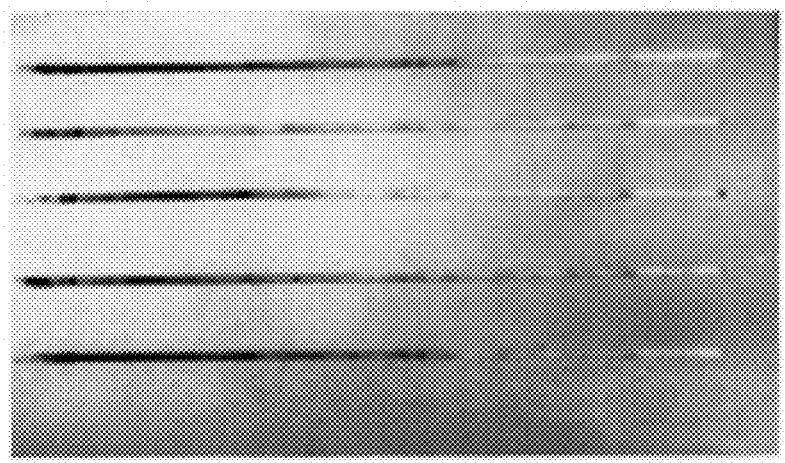
FIG. 1 is the treatment results on day 14, in which from the top to the bottom, the graphs are.
Figure 2:
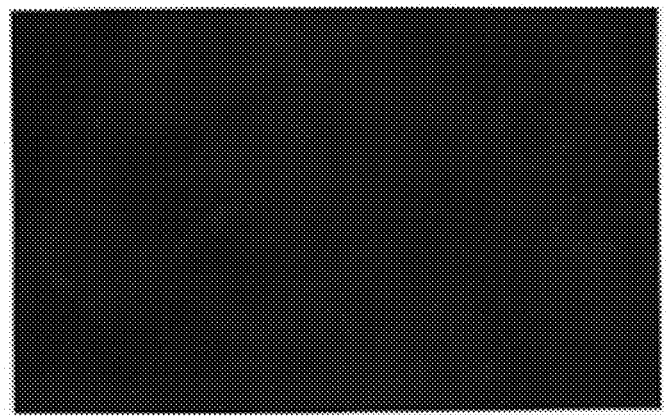

FIG. 2 shows the fluorescence intensity of ANA decreases ×200, when treated with chlorogenic acid (high dose) for 14 days.

Figure 3:
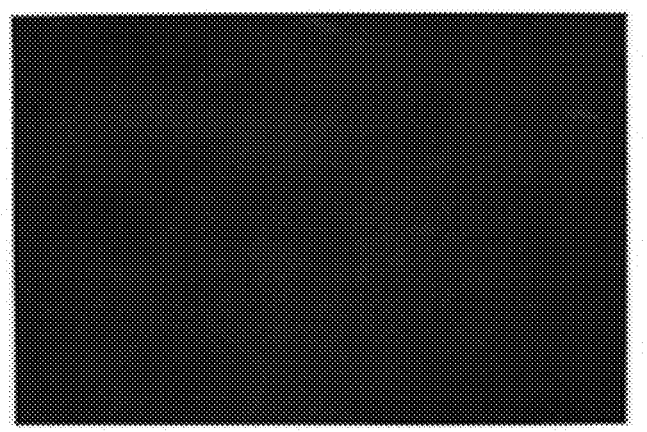

FIG. 3 shows the fluorescence intensity of ANA decreases ×200, when treated with chlorogenic acid (high dose) for 21 days.

Figure 4:
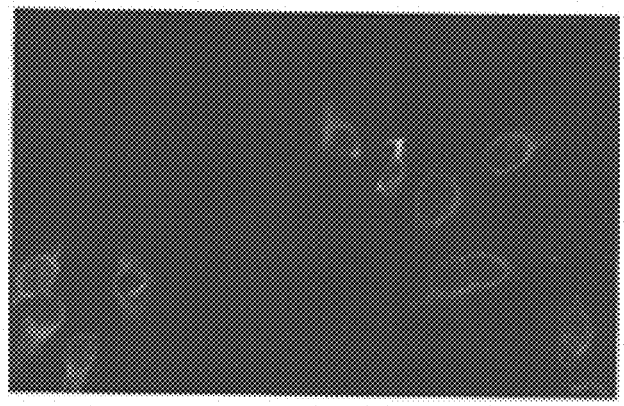

FIG. 4 shows the fluorescence intensity of ANA decreases ×200, when treated with chlorogenic acid (high dose) for 28 days.

Figure 5:
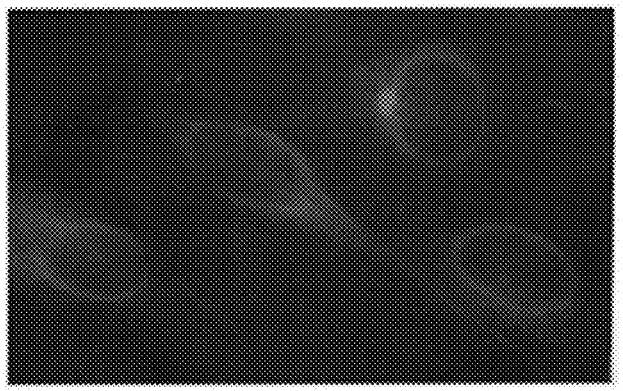

FIG. 5 shows the fluorescence intensity of ANA doesn't decrease ×200, when treated with artesunate for 28 days.

Figure 6:
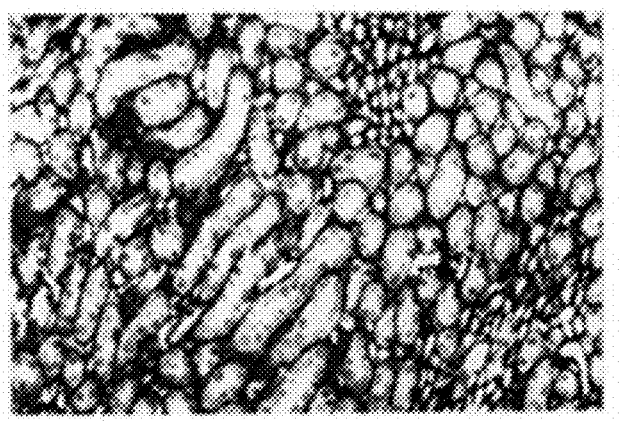

FIG. 6 is the kidney slices of normal mice, showing that the renal tubular basement membrane in renal medullahas a small amount of silver staining (×5).

Figure 7:
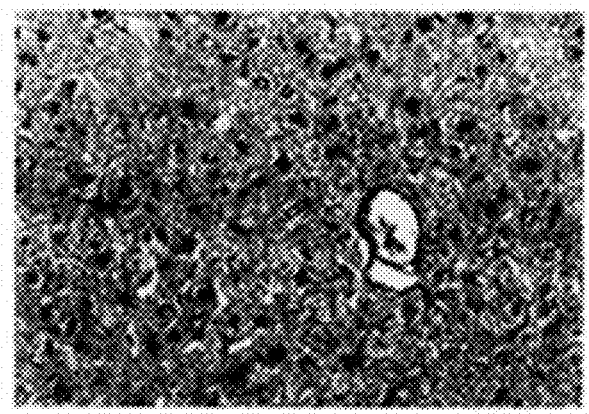

FIG. 7 shows that in model mice treated by LPS via ip for 14 days, the basilar membrane of hepatic blood vessels increased thickness (×50).

Figure 8:
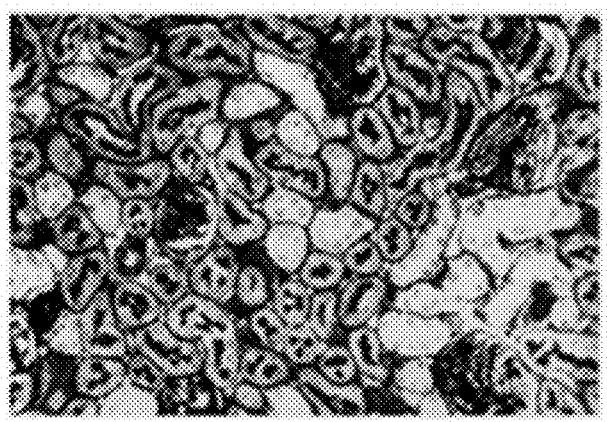

FIG. 8 shows that when treated by high dose of chlorogenic acid for 28 days, kidney glomerulus volume of mice swells and cell numbers increase, compared with the normal, while the thickening degree of renal glomerulus and tubular basement membrane reduces (×50), compared with the normal mice.

Figure 9:

FIG. 9 shows that in the group treated with artesunate for 28 days, the glomerular basement membrane increased thickness (×50), compared with the normal mice.

Figure 10:

FIG. 10 shows that in the group treated with prednisone for 28 days, the glomerular basement membrane obviously increased thickness (×50), compared with the normal mice.

Figure 11:
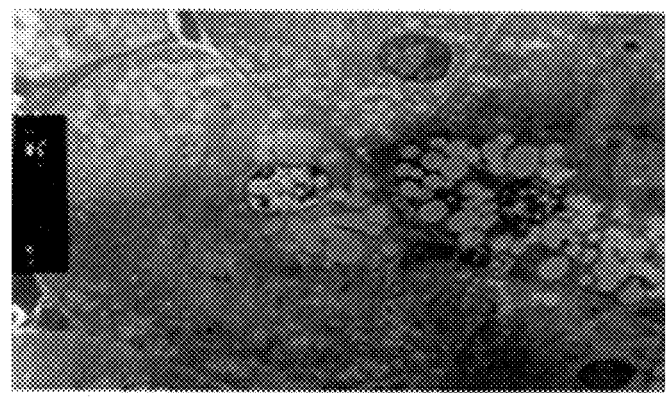

FIG. 11 shows in the 24 h model mice, glomerular capsule wall epithelial cells severely proliferate, producing mononuclear cells, and mitochondria greatly increase (×3000).

Figure 12:
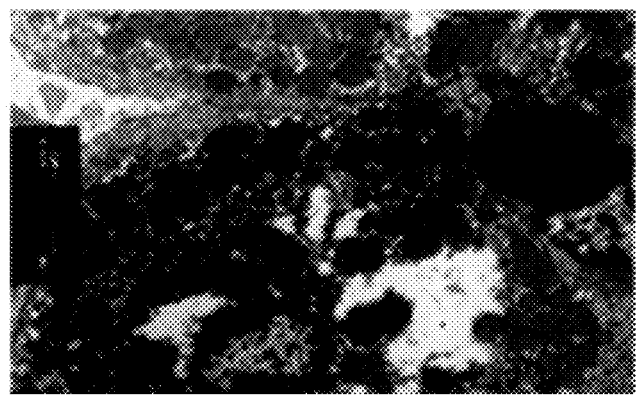

FIG. 12 shows in the 28 d model mice, the proliferative degree of glomerular capsule wall epithelial cells decreases, having mononuclear cells, and the number of mitochondria is large (×6600).

Figure 13:
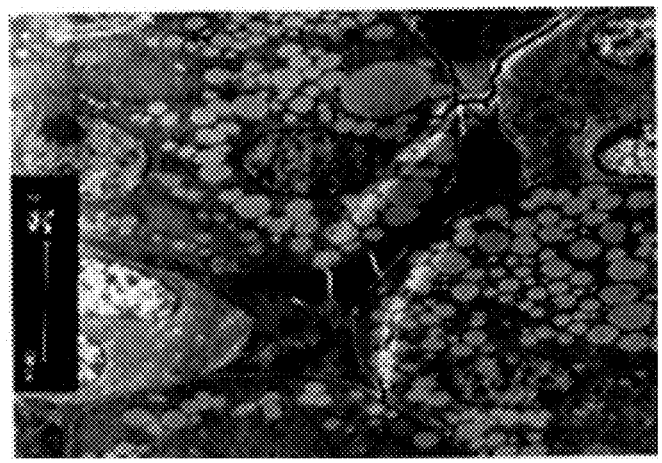

FIG. 13 shows that in the high-dose group of chlorogenic acid treated by 21 days, the proliferative degree of glomerular capsule wall epithelial cells somewhat relieves (×4000).

Figure 14:
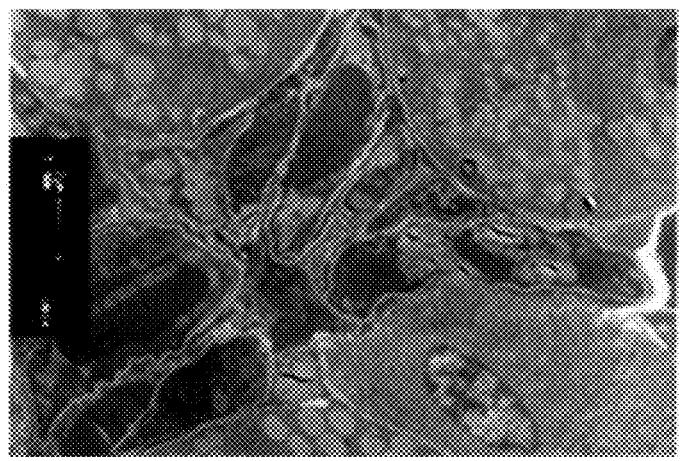

FIG. 14 shows that in the group treated with artesunate for 21 days, the proliferative degree of glomerular capsule wall epithelial cells slightly relieves, but the relieving degree is smaller than the Qingteng capsule group, accompanied by thrombus (×3000).

Figure 15:
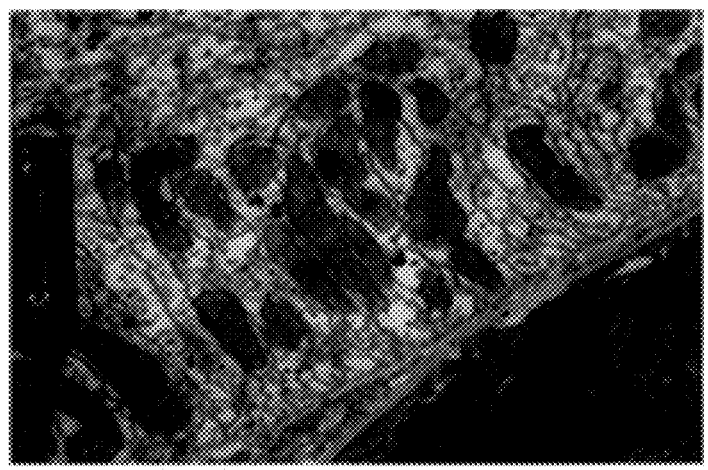

FIG. 15 shows that in the group treated with prednisone for 21 days, the proliferative degree of glomerular capsule wall epithelial cells slightly relieves compared with the model group, but the relieving degree is smaller than the Qingteng capsule group, accompanied by the increased number of mitochondria (×12500).

EXAMPLES

Example 1: Study on the In Vivo Pharmacodynamic Experiment of Chlorogenic Acid Treating Lupus Erythematosus 1. Materials and Methods 1.1 Animals 5-7 weeks BALB/c mice, weighing 17.0-21.0 g, half male and half female, are provided by the Experimental Animal Center of Sichuan University.

Medicines

Chlorogenic acid is provided by Sichuan Jiuzhang Biochemical Science and Technology Development, Co. Ltd, the content of chlorogenic acid is 99.20%, with a batch number: 131101. During investigation, high, middle, and low concentrations of normal saline were prepared for use. Prednisone is manufactured by Zhejiang Xianju Pharmaceutical Co., Ltd, 5 mg/tablet, with a a batch number: 110502; *Escherichia coli* lipopolysaccharide is produced by Sigma, with Lot58kp8725, and prior to use, the lipopolysaccharide is prepared as 0.25 g/L using normal saline. HEP-2 cell sheets are produced by Scimedx company. Fluorescein-labeled goat-anti-mouse serum (FITC Goat Anti-Mouse IgG) is purchased from Vector company. ENA polypeptide immunoblotting membrane is available from Shenzhen Hengjia company. Biotin goat anti-mouse serum (biotin goat anti-mouse IgG) is from Vector company. Horseradish peroxidase-avidin (HRP-avidin) conjugates are obtained from Vector company.

Apparatus

Ultraviolet lamp (30 W) is produced by Shanghai Special Lamp Factory, with a maximal energy spectrum of 312 nm, an energy of 2.0 Mj/cm$^2$, a distance of 30 cm, in which UVB part occupies above 60% quantity of radiant energy; Olympus BH-2 universal microscope is manufactured by Olympus company, Japan; Philips M800 transmission electron microscope is produced by Philips company, Netherlands.

Methods

The back of mice was shaved and acutely exposed to Ultraviolet of 2 h/d*3 d, with a distance of 30 cm. After exposure to UV, 2.5 mg/kg of LPS was administrated once by ip, and after 24 h, the model was successfully established; the mice in the normal control group received normal saline via ip. 24 h after injection of LPS (ip), medicines were given to the model mice by intragastric administration. Chlorogenic acid test groups received high, middle, and low doses of medicines, by intragastric administration at a respective dosage of 10 mg/kg*d, 20 mg/kg*d, and 40 mg/kg*d. The positive control group A received 2 mg/kg*d of artesunate by stomach perfusion, while the positive control group B received 1 mg/kg*d of prednisone by stomach perfusion. Mice in the model and normal control group all received 0.4 ml/mouse normal saline by gavage. After 15 days of administration, animals in each group were taken blood by separating eyeballs on days 14, 21, 28, and after cultured in water bath at 37° C. for 1 h, the blood sample was centrifugated at 2000 r/min for 5 min, to draw serum for use. On day 21, after blood collection, animals were sacrificed by dislocation, followed by collection of liver and kidney, and they were placed in fixative solutions of electron microscope and light microscrope, respectively.

Serologic Detection

Serum of mice was diluted at 1:100 with special buffer solution of Shenzhen Hengjia, and then 200 μL of diluted serum was respectively added to the reactive tank with corresponding number, cultured in the incubator at 37° C. for 30 min, and washed with the buffer solution four times, 2 min for each time; 200 μL of diluted biotin goat anti-mouse IgG (1:100) was added, cultured in the incubator at 37° C. for 30 min, and then washed with the buffer solution four times, 2 min for each time; 100 μL of diluted HRP-avidin (1:100) was added, cultured in the incubator at 37° C. for 30 min, and then washed as mentioned-above; reactive solutions A and B were added till appearance of positive bands, then washed with the buffer solution. Compared with the standard bands of ENA polypeptide antibody spectrum in the same kit, if the positive bands appeared at 28/29,13.5 ku polypeptide; 15,16.5,38 kupolypeptide; 52 kupolypeptide and 47/48,45 kupolypeptide, that can be determined as anti-Sm, anti-Rib, anti-ssA, and anti-ssB positive antibody. Serum was diluted with PBS at 1:40, then 20-30 μL of diluted serum was dropped into the scrobiculus of HEp-2 cell sheets, each cell sheet for each group. In the process of dropping serum, it should be noted that the surface of cell sheet can not be touched. After addition of serum, cell sheet was placed in wet box and kept for 30 min at room temperature (25° C.). After 30 min, the cell sheet was taken out, and serum was carefully washed out with PBS, then carefully washed twice with PBS, 5 min for each time; after washing, the remained PBS was removed by special absorbent paper of Scimedx company (In this process, it should be noted that becoming dry of cell substrates will affect the results). 20-30 μL of diluted (PBS, 1:100) FITC goat anti-mouse IgG was added by dropping, and then incubated in wet box at room temperature for 30 min. After washing with PBS, steps were same to above. The remained PBS was removed by absorbent paper, and 1-2 drops of fluorescent mounting media were added to the cell sheet. The cover glass was mounted, observed under Olympus BH-2 universal microscope, and then photographed.

Preparation of Triple Stained Sample

On day 21, triple staining was carried out, and the sample used for observation under light microscope was fixed in 10% formalin, then dehydrated, cleared, waxdipped, and embedded, for slicing. The thickness of slice is 3 μm, and at beginning of staining, wax was routinely deprived to water. After oxidation with 0.5% periodic acid, the slice was macerated in hexamine silver fluid for about 2 h (constant temperature 58° C.), washed with distilled water, dyed with hematoxylin for 1 min. After washing with water, the slice was dyed by dropping the ponceau staining solution for 5 min, differentiated with 70% ethanol, dehydrated with gradient ethanol, cleared with xylene, and sealed with neutral gum.

Preparation of Electron Microscope Sample

On day 21, the sample used for observation under electron microscope was fixed in mixed stationary solution of 2% paraformaldehyde+0.25% glutaral for 4 h, rinsed with TBS, treated with 1% osmic acid, followed by fixation for 1 h, rinsed with buffer solution, dehydrated with acetone, dyed with uranyl acetate for 2 h, macerated in Epon812 and embedded, and cut into slices with LEICA ultramicrotome. The slices were stained with lead solution, and the sample was observed under transmission electron microscope when it was dry.

Results 2.1 Animal Death Conditions 24 h after 60 animals received LPS via ip, 6 animals were dead, three females and three males. After that, there were no death of animals in each drug group and each control group till day 28 of drug administration.

Serologic Detection Results

When treated for 14 days, 21 days, and 28 days, the detection results of ENA polypeptide body and ANA in serum collected from animals are listed in Tables 1-3 shown in FIGS. 1-5; there is no sex differences in results of each group.

TABLE 1

Detection results of ENA polypeptide body and ANA on day 14

| Serologic Results | Chlorogenic acid | | | Artesunate | Prednisone | Control group | |
|---|---|---|---|---|---|---|---|
| | High | Middle | Low | | | Model | Normal |
| Anti-Sm | (+) | (+) | (+) | (+) | (+) | (+) | (−) |
| Anti-Rib | (+) | (+) | (+) | (+) | (+) | (+) | (−) |
| Anti-ssA | (+) | (+) | (+) | (+) | (+) | (+) | (+) |
| Anti-ssB | (+) | (+) | (+) | (+) | (+) | (+) | (+) |
| ANA | (+++) | (+++) | (++++) | (++++) | (++++) | (++++) | (−) |

(+): positive
(−): negative
(++++): intenseintensity
(+++): stronger fluorescent intensity.

TABLE 2

Detection results of ENA polypeptide body and ANA on day 21

| Serologic Results | Chlorogenic acid | | | Artesunate | Prednisone | Control group | |
|---|---|---|---|---|---|---|---|
| | High | Middle | Low | | | Model | Normal |
| Anti-Sm | (+) | (+) | (+) | (+) | (+) | (+) | (−) |
| Anti-Rib | (+) | (+) | (+) | (+) | (+) | (+) | (−) |
| Anti-ssA | (+) | (+) | (+) | (+) | (+) | (+) | (−) |
| Anti-ssB | (+) | (+) | (+) | (+) | (+) | (+) | (+) |
| ANA | (++) | (++) | (+++) | (+++) | (+++) | (++++) | (−) |

(+): positive
(−): negative
(++++): intense fluorescence
(+++): stronger fluorescence
(++): weeker fluorescence.

TABLE 3

Detection results of ENA polypeptide body and ANA on day 28

| Serologic Results | Chlorogenic acid | | | Artesunate | Prednisone | Control group | |
|---|---|---|---|---|---|---|---|
| | High | Middle | Low | | | Model | Normal |
| Anti-Sm | (+) | (+) | (+) | (+) | (+) | (+) | (−) |
| Anti-Rib | (−) | (−) | (+) | (−) | (+) | (+) | (−) |
| Anti-ssA | (−) | (+) | (+) | (+) | (+) | (+) | (−) |
| Anti-ssB | (−) | (+) | (+) | (+) | (+) | (+) | (−) |
| ANA | (++) | (++) | (+++) | (+++) | (+++) | (++++) | (−) |

(+): positive
(−): negative
(++++): intensefluorescence
(+++): stronger fluorescence
(++): weeker fluorescence.

Observation Results of Triple Staining Results

On day 21, pathological section showed: (1) For the normal control mice, the renal glomerular basement membrane of kidney substantiacorticalis has a small amount of silver staining, and the renal tubular basement membrane also has a small amount of silver staining, and the renal tubules in the structure of substantiamedullarish as a small amount of silver staining; the basilar membrane of hepatic blood vessels was not found to thicken. (FIG. 6). (2) On day 21, for model mice, silver staining results showed the volume of kidney glomerulus augmented, the cellular numbers increased, accompanied by mononuclear cells appearing by the side of kidney glomerulus, infiltration of chronic inflammatory cells into kidney glomerulus and interstitial substance, and renal glomerular and tubular basement membrane obviously thickened compared with normal mice; the basilar membrane of hepatic blood vessels increased thickness, compared with normal mice. (FIG. 7). (3) When administration of chlorogenic acid for 21 days, the tissue structure of mouse kidney can still be seen, renal glomerular volume swelled compared with the normal mice, cell numbers increased, chronic inflammatory cells infiltrated into kidney glomerulus and interstitial substance, the basilar membrane of renal glomerulus and tubule increased thickness compared with normal mice; but the conditions were better than the model group, especially for the high dose group. (FIG. 8). (4) For the group treated with artesunate for 21 days, the basilar membrane of renal glomerulus and tubule increased thickness compared with the normal mice. (FIG. 9). (5) For the group treated with prednisone for 21 days, the basilar membrane of renal glomerulus and tubule also increased thickness compared with the normal mice. (FIG. 10).

2.4 Observation Results of Electron Microscope Samples

Observation results of electron microscope showed (1) For the normal mice, renal glomerular capsule wall epithelial cells did not proliferate, and the number of mitochondria was normal; (FIG. 11) (2) For the model mice, on the day 21, renal glomerular capsule wall epithelial cells severely proliferated, producing mononuclear cells, and the number of mitochondria greatly increased. (FIG. 12) (3) After administration of chlorogenic acid for 21 days, the proliferative degree of renal glomerular capsule wall epithelial cells somewhat relieved, and the release degree in high dose group was the most obvious; (FIG. 13) (4) For the group treated with artesunate for 21 days, the proliferative degree of renal glomerular capsule wall epithelial cells somewhat relieved compared with the model group, but the relieving degree is smaller than the chlorogenic acid treatment group, accompanied by thrombus; (FIG. 14) (5) in the group treated with prednisone for 21 days, the proliferative degree of renal glomerular capsule wall epithelial cells somewhat relieved compared with the model group, but the relieving degree is smaller than the chlorogenic acid treatment group, and the number of mitochondria increased, accompanied by the loss of organelles. (FIG. 15)

3. Conclusion

Pharmacodynamic investigation of chlorogenic acid carried out by this model shows: (1) From the serologic detection results, it can be seen that the model is successfully made. (2) The investigation results of triple staining samples show: For the model mice, at 24 h, from silver staining results, it can be seen that the volume of kidney glomerulus augmented, the cellular numbers increased, chronic inflammatory cells infiltrated into kidney glomerulus and interstitial substance, renal glomerular and tubular basement membrane obviously thickened compared with normal mice; the basilar membrane of hepatic blood vessels increased thickness, compared with normal mice. On days 2, 3, 7, 14, and 21, it also can be seen that the volume of kidney glomerulus swelled, the cellular numbers increased, chronic inflammatory cells infiltrated into kidney glomerulus and interstitial substance, accompanied by obvious thickening of renal glomerular and tubular basement membrane compared with normal mice; the basilar membrane of hepatic blood vessels increased thickness. For the chlorogenic acid group administrated for 28 days, renal glomerular volume also swelled, cell numbers increased, but the thickening degree of renal glomerular and tubularbasilar membrane reduced compared with normal mice, silver staining weekened, and the staining of hepatic blood vessel basilar membrane also somewhat recovered. (3) Investigation results of electron microscope samples also show that for the normal mice, renal cells and renal glomerular capsule wall epithelial cells did not proliferate, and the number of mitochondria was normal; for the 24 h model mice, renal cells and renal glomerular capsule wall epithelial cells severely proliferated, producing mononuclear cells, and the number of mitochondria greatly increased. After administration of chlorogenic acid for 21 days, the proliferative degree of renal glomerular capsule wall epithelial cells somewhat relieved, and the release degree in high dose group was the most obvious;

Above experimental results indicate chlorogenic acid has good therapeutic effect on lupus erythematosus. Its mechanism of action may be by improving immune functions of mice with lupus erythematosus.

The invention claimed is:

1. A method for treating lupus erythematosus comprising administering an effective amount of a pharmaceutical composition to a subject in need thereof, wherein the pharmaceutical composition comprises chlorogenic acid and is administered at a dosage of 1-100 mg/kg per day.

2. The method according to claim 1, wherein the pharmaceutical composition improves the immune function.

3. The method according to claim 1, wherein the pharmaceutical composition further comprises pharmaceutically acceptable excipients or auxiliary materials.

4. The method according to claim 1, wherein the pharmaceutical composition is administered orally, topically, transdermally, or by injection.

5. The method according to claim 1, wherein the pharmaceutical composition further comprises a compound treating lupus erythematosus.

6. The method according to claim 1, wherein the compound treating lupus erythematosus is selected from the group consisting of hydroxychlorochin, methopterin, azathioprine, clofazimine, thymosin, levamisole, and thymosin.

7. The method according to claim 1, wherein the pharmaceutical composition is administered at a dosage of 40-100 mg/kg per day.

8. The method according to claim 7, wherein the pharmaceutical composition is administered for at least 15 days.

* * * * *